(12) United States Patent
Watanabe (10) Patent No.: US 7,029,454 B2
(45) Date of Patent: Apr. 18, 2006

(54) MILKING DEVICE

(75) Inventor: Toshi Watanabe, Tokyo (JP)

(73) Assignee: Nihon University, Tokyo (JP)

( * ) Notice: Subject to any disclaimer, the term of this patent is extended or adjusted under 35 U.S.C. 154(b) by 0 days.

(21) Appl. No.: 10/477,206

(22) PCT Filed: May 15, 2002

(86) PCT No.: PCT/JP02/04698

§ 371 (c)(1),
(2), (4) Date: Nov. 18, 2003

(87) PCT Pub. No.: WO02/094345

PCT Pub. Date: Nov. 28, 2002

(65) Prior Publication Data

US 2004/0133151 A1      Jul. 8, 2004

(30) Foreign Application Priority Data

May 18, 2001 (JP) ............................. 2001-149458

(51) Int. Cl.
*A61M 1/06* (2006.01)
(52) U.S. Cl. ...................................... 604/74
(58) Field of Classification Search ................. 604/74, 604/75, 35–38, 132, 133, 346
See application file for complete search history.

(56) References Cited

U.S. PATENT DOCUMENTS

| | | | | |
|---|---|---|---|---|
| 50,457 A | * | 10/1865 | Colrin ........................... | 604/74 |
| 1,596,520 A | * | 8/1926 | Eskholme et al. ........ | 119/14.33 |
| 1,670,610 A | * | 5/1928 | Woodard ...................... | 604/74 |
| 4,263,912 A | * | 4/1981 | Adams ......................... | 604/75 |
| 4,323,067 A | * | 4/1982 | Adams ......................... | 604/74 |
| 4,583,970 A | * | 4/1986 | Kirchner ....................... | 604/74 |
| 4,680,028 A | * | 7/1987 | Stuart ........................... | 604/74 |
| 4,772,262 A | * | 9/1988 | Grant et al. ................... | 604/74 |
| 4,794,915 A | * | 1/1989 | Larsson ....................... | 601/153 |
| 4,799,922 A | * | 1/1989 | Beer et al. .................... | 604/74 |
| 4,857,051 A | * | 8/1989 | Larsson ....................... | 604/74 |
| 4,886,494 A | | 12/1989 | Morifuji | |
| 5,100,406 A | * | 3/1992 | Panchula ...................... | 604/74 |
| 5,720,722 A | * | 2/1998 | Lockridge .................... | 604/74 |

(Continued)

FOREIGN PATENT DOCUMENTS

JP       36-493       1/1961

(Continued)

OTHER PUBLICATIONS

U.S. Appl. No. 09/715,990, filed Nov. 17, 2000.*

(Continued)

*Primary Examiner*—Sharon Kennedy
(74) *Attorney, Agent, or Firm*—Oblon, Spivak, McClelland, Maier & Neustadt, P.C.

(57) ABSTRACT

Provided is a breast pump for the mother's milk, which makes it possible to obtain universal milk expression data without being affected by an individual difference, for example. The breast pump is composed of a collection container, a milk expressing member, and a negative pressure source for producing pulsated negative pressure. The milk expressing member is provided at an end with a teat cup and at an opposite end with a connector plug to the negative pressure source. The milk expressing member is divided by a partition plate. A flexible teat cup liner is replaceably fitted in the teat cup, and configured to be brought into contact with an areola and nipple of a breast.

7 Claims, 4 Drawing Sheets

U.S. PATENT DOCUMENTS

| | | | |
|---|---|---|---|
| 5,885,246 A * | 3/1999 | Ford | 604/74 |
| 6,090,065 A * | 7/2000 | Giles | 604/74 |
| 6,273,868 B1 * | 8/2001 | Nordvik | 604/74 |
| 6,383,163 B1 * | 5/2002 | Kelly et al. | 604/74 |
| 6,383,164 B1 * | 5/2002 | Johansen et al. | 604/74 |
| 6,579,258 B1 * | 6/2003 | Atkin et al. | 604/74 |
| 6,663,587 B1 * | 12/2003 | Silver et al. | 604/74 |
| 6,673,036 B1 * | 1/2004 | Britto | 604/74 |
| 6,706,012 B1 * | 3/2004 | McKendry et al. | 604/74 |
| 2003/0149398 A1 * | 8/2003 | Renz et al. | 604/74 |
| 2004/0133151 A1 * | 7/2004 | Watanabe | 604/74 |

FOREIGN PATENT DOCUMENTS

| | | |
|---|---|---|
| JP | 103143/1986 | 7/1986 |
| JP | 72543/1987 | 5/1987 |
| JP | 3-62106 | 9/1991 |
| JP | 4-329942 | 11/1992 |
| JP | 7-194691 | 8/1995 |
| JP | 11-178917 | 7/1999 |
| JP | 2000-511443 | 9/2000 |
| WO | 97/04822 | 2/1997 |

OTHER PUBLICATIONS

Normal Breasts Gallery, "Have You Seen Pictures of Normal Non-Sexual Breasts?", www.007b.com/breast_gallery.php, copyright 2003-2005, pp. 1-16.*

Breast Pump Accessories, www.breastfeedingaccessories.com, copyright 2002-2003, pp. 1-16.*

Spangler, Amy "Common Breastfeeding Problems: Sore Nipples", www.breastfeeding.com/all_about/all_about_sore.html, copyright? 1998-2005, pp. 1-4.*

* cited by examiner

MILKING DEVICE

REFERENCE TO RELATED APPLICATIONS

This application is a 371 of PCT/JP02/04698 filed May 15, 2002.

TECHNICAL FIELD

This invention relates to breast pumps, and particularly to breast pumps suited for collecting human milk in a standardized manner.

BACKGROUND ART

In recent years, effects of contamination of mothers' milk especially by dioxins, which are carcinogens, endocrine-disrupting chemicals and the like on infants have given rise to a serious social concern throughout the world. A great majority of these contaminants led by dioxins and including endocrine-disrupting chemicals are soluble in fat so that, once they are uptaken in the body, they are mostly stored in adipose tissues although extremely small fractions of them are discharged into excrement via bile. As body fat is mobilized upon synthesis of milk fat in the mammary glands, the contaminants stored in the fatty tissues transfer into milk. As a result, milk acts as a principal discharge route for contaminants led by dioxins and including endocrine-disrupting chemicals. Collection of human milk in a standardized method is, therefore, a useful means for the detection of these exogeneous toxic substances. Further, milk expression or suction becomes necessary for the purpose of treatment if any morbid abnormality is observed in the quality of milk for one reason or another and breast feeding has to be discontinued or if an intrammary accumulation of any non-milk morbid product is ascertained.

It is, however, the current circumstances that no useful breast pump is available for the collection of human milk in a standardized universal manner and expression of milk is manually conducted at every medical institution. Hence, collection of human milk is hardly considered to be performed adequately in a standardized universal manner. For example, the pulsating suction breast pump disclosed in JP-A-11-178917 includes a teat cup secured on a free end of a cylinder such that a suction pressure is intermittently produced within the teat cup by reciprocations of a piston. However, this breast pump is complex in mechanism, has difficulty in adjusting the pulsation cycle, and lacks flexibility. Further, it is difficult to disassemble and wash this breast pump, and moreover, it is essential to use a sealing packing in direct contact with a milk expressing passageway. There is, accordingly, a potential risk that the sealing packing may become a cause of bacterial growth unless thorough washing is conducted.

In the breast pump which is disclosed in JP-A-2000-511443 and is capable of double-breast pumping, a reduced pressure is periodically produced by a mechanism equipped with a diaphragm pump instead of a piston-cylinder means so that this breast pump is simplified to some extent in mechanism. However, a milk expressing member which is attached to a collection container is of a type that the milk expressing member is provided at a lower extremity thereof, where the milk expressing member is inserted into the collection container, with an on/off valve, and has a construction such that at the time of a reduced pressure, the interior of a teat cup is brought into a state reduced in pressure and the on/off valve is closed but at the time of atmospheric pressure, the on/off valve is opened by the expressed human milk to collect it in the collection container. In addition to a need for a complex mechanism for the assembly of the on/off valve, it is necessary to arrange within the milk expressing member such a complex partition that upon expressing milk, permits passage of air therethrough but does not permit passage of human milk to the side of the diaphragm pump. Therefore, it is difficult to wash the inside of the milk expressing member, and moreover, the on/off valve involves a potential risk that it may become a cause of bacterial growth.

Further, these breast pumps are each of the construction that the inner wall of the teat cup is brought in its entirety into direct contact with the breast to directly apply a negative pressure there. A stimulation by the negative pressure is, therefore, different from a suckling stimulation by an infant, that is, an actual suckling stimulation which acts only on the areola and nipple of the mother's breast, and moreover, expression of milk is not considered to proceed smoothly.

With the foregoing circumstances in view, the object of the present invention is to provide a novel breast pump, which permits universal expression of milk from the human breast without being affected by a personal difference of a person who performs the expression of milk. In addition, the another object of the present invention is to provide a novel breast pump, which is simple in construction, permits easy washing of the inside of a milk expressing member, and can avoid inconveniences such as bacterial growth. Furthermore, the further object of the present invention is to provide a novel breast pump, which is designed to permit an application of similar stimulations as suckling stimulations by an infant to the areola and nipple of the mother's breast so that smooth expression of milk can be performed.

DISCLOSURE OF THE INVENTION

A breast pump according to the present invention is characterized in that the breast pump includes a collection container, a milk expressing member attachable to said collection container, and a negative pressure source for producing a negative pressure such that a pressure is periodically pulsated at constant intervals between the negative pressure and atmospheric pressure; the milk expressing member is provided at an end thereof with a teat cup, at an opposite end thereof with a connector plug to the negative pressure source, and between the teat cup and the connector plug with a passageway to the collection container; a partition plate is arranged in the passageway to divide the milk expressing member into a space communicated to the teat cup and a space communicated to the connector plug; and a teat cup liner is replaceably fitted in the teat cup, wherein the teat cup liner is dimensioned to be brought into contact with an areola and nipple of a breast and has such flexibility and resiliency that the teat cup liner undergoes a deformation toward the teat cup when exposed to the negative pressure but restores an initial shape thereof when exposed to the atmospheric pressure.

Figure 1:
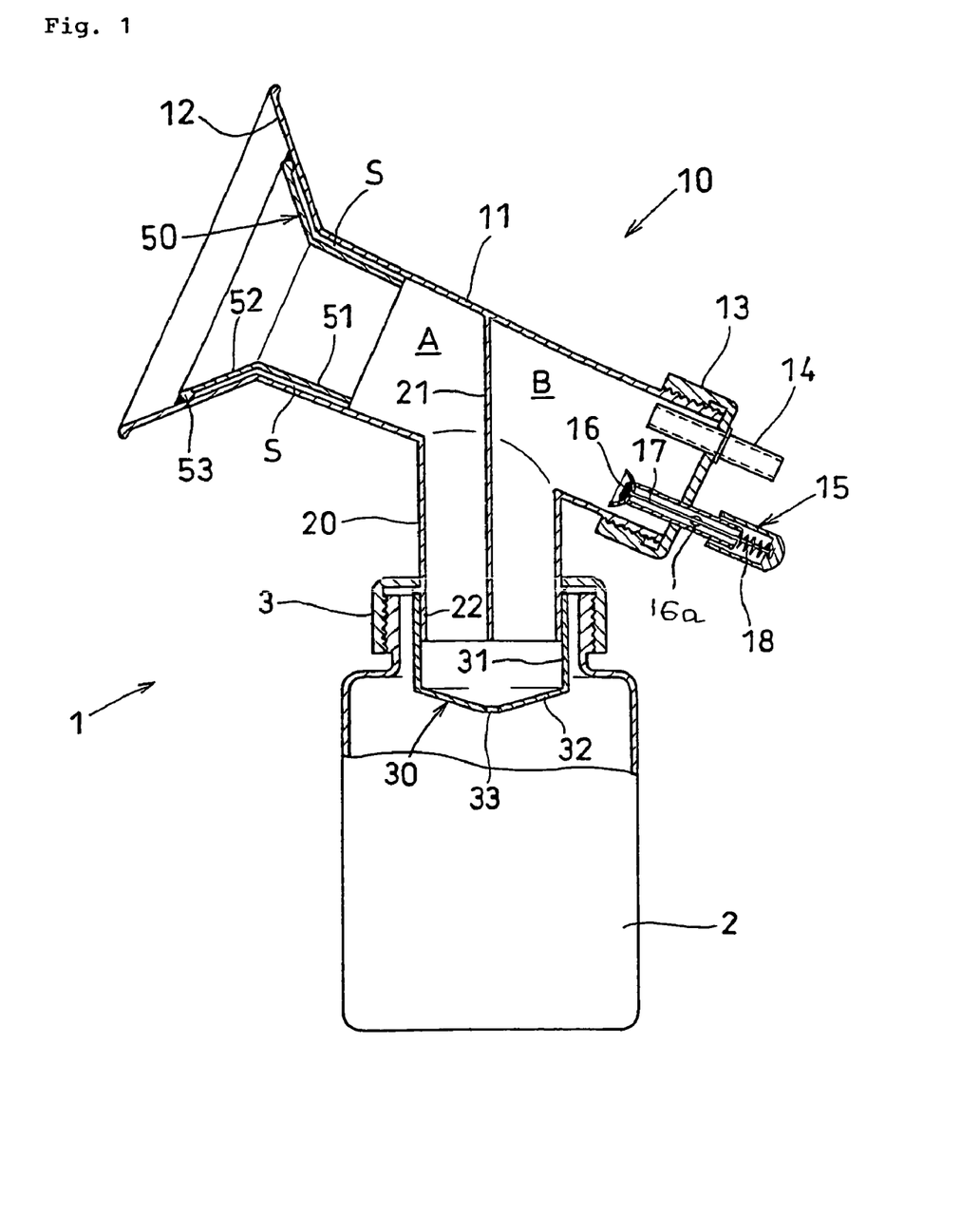
FIG. 1 is a cross-sectional view illustrating a breast pump according to the present invention.
Figure 2:
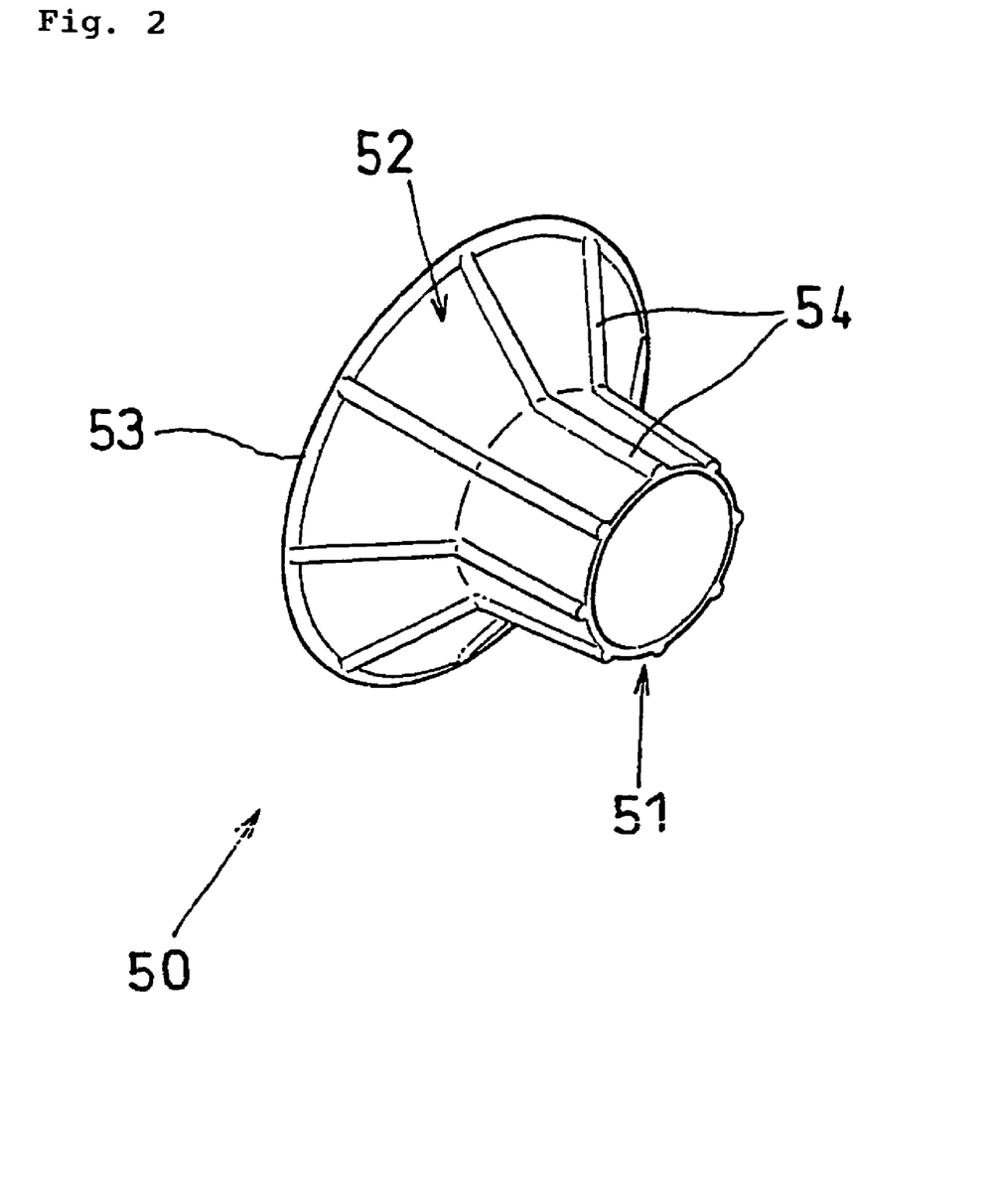
FIG. 2 is a perspective view illustrating a teat cup liner for use in the breast pump according to the present invention.
Figure 3:
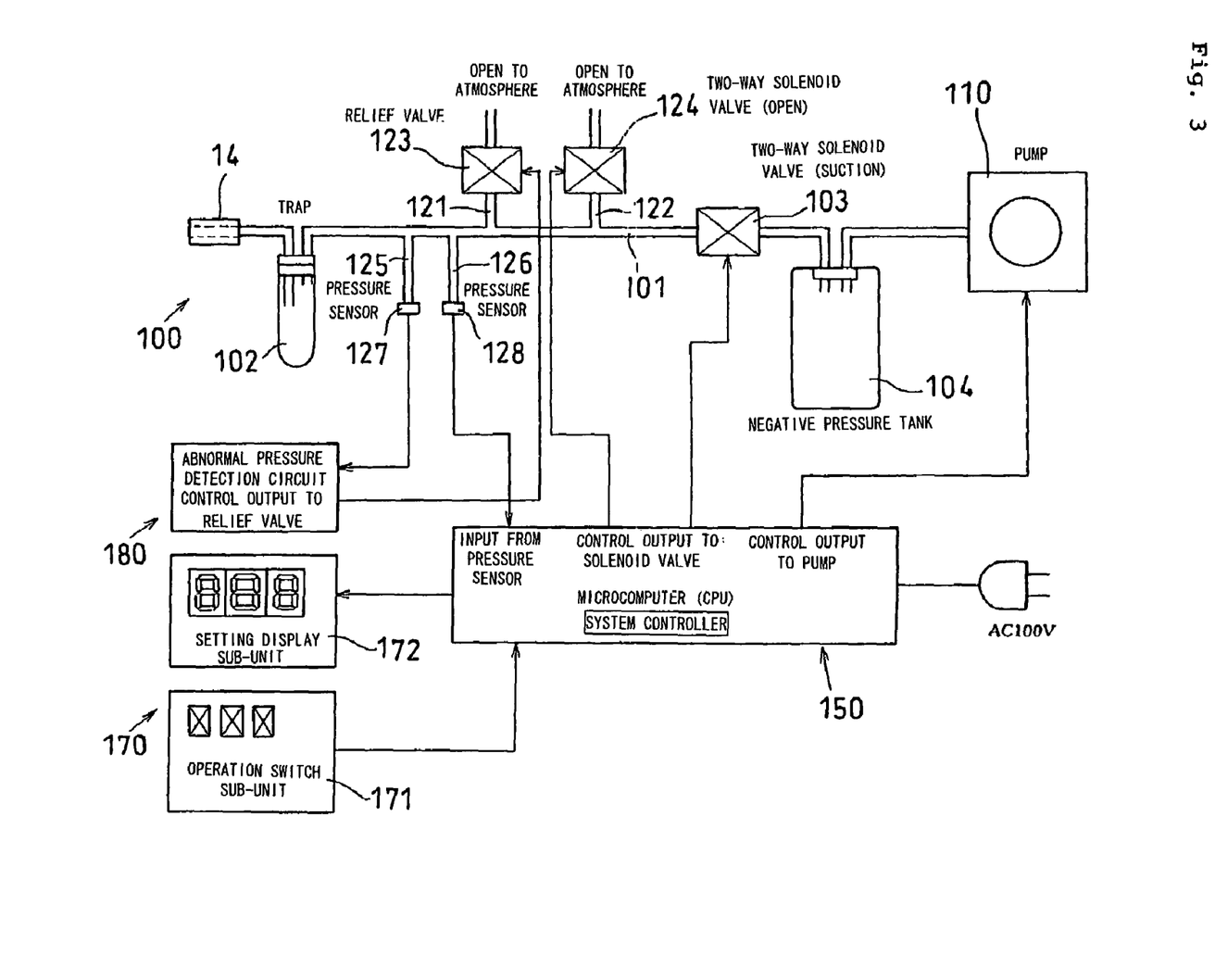
FIG. 3 is a diagram illustrating one example of a negative pressure source according to the present invention.

The signs in the drawings indicate the following elements: 1: breast pump, 2: collection container, 10: milk expressing member, 11: main body section in a cylindrical form, 12: teat cup, 13: end cover, 14: connector plug, 15: relief valve, 20: branch tube, 21: partition plate, A: space communicated to a side of the teat cup, B: space communicated to the connector plug, 30: cap, 33: small aperture, 50: teat cup liner, 51: insert portion, 52: conical portion, 53: thickened annular portion, 54: ridges, S: air cells sealed on a side of forward ends thereof by the thickened annular portion and open on a side of rear ends thereof to the space A, 100: negative pressure source, 110: vacuum pump, 150: computer.

BEST MODES FOR CARRYING OUT THE INVENTION

No particular limitation is imposed on the negative pressure source insofar as it can produce a negative pressure such that a pressure is periodically pulsated at constant intervals between the negative pressure and atmospheric pressure. It is, however, preferred to use a negative pressure source of such a construction that the negative pressure source is provided at least with a vacuum pump, a line for connecting the vacuum pump with the connector plug of the milk expressing member, a first two-way solenoid valve arranged on the line, a branch line arranged on the line on a side upstream of the first two-way solenoid valve, a second two-way solenoid valve arranged on the branch line, and a system controller for controlling on/off of at least the solenoid valves; and that the branch line is open at a free end thereof to an atmosphere.

The breast pump is extremely simplified in construction because inside the milk expressing member, there is only the partition plate which divides the interior into a space communicated to the teat cup and a space communicated to the connector plug. As the partition plate is located in the section of the passageway to the collection container, the interior can be easily cleaned by inserting a brush or the like from the side of the teat cup or through the end portion on the side of the connector plug. Periodical negative pressures and atmospheric pressures from the negative pressure source are transmitted to the side of the teat cup through the collection container, so that expression of milk can be performed without any trouble.

Fitted in the teat cut is the teat cup liner, which is dimensioned to be brought into contact with the areola and nipple of the mother's breast and has such flexibility and resiliency that the teat cup liner undergoes a deformation toward the teat cup when exposed to the negative pressure but restores its initial shape when exposed to the atmospheric pressure. Stimulations similar to suckling stimulations by an infant can, therefore, be applied to the areola and nipple of the mother's breast by causing the periodical negative pressures and atmospheric pressures from the negative pressure source to act on the teat cut liner. These stimulations enable smooth and adequate expression of milk. The teat cup liner is replaceable, so that provision of teat cup liners of different sizes in advance makes it possible to perform appropriate expression of milk from breasts of different sizes and shapes by simply replacing the teat cup liner.

When a negative pressure source having at least a vacuum pump, two two-way solenoid valve and a system controller is used as the negative pressure source, stable expression work of milk can be performed under computer control and further, with the same breast pump, expression of milk can be conducted in an optimal state under a number of different conditions.

Preferably, a cap, which is provided at a tip thereof with a small aperture capable of performing a function as a check valve, is detachably mounted on an outlet portion of the passageway of the milk expressing member to the collection container. Use of such a cap can prevent milk, which has been collected in the collection container, from flowing backward toward the side of the milk expressing member in such a case that the breast pump accidentally falls down during or after the expression of milk. The diameter of the small aperture which can perform a function as a check valve may preferably be from 1 mm to 9 mm or so. In an experiment, arrangement of a cap simply having a small aperture of such a dimension successfully prevented a reverse flow by making effective use of properties which the mother's milk has as a liquid, such as the surface tension and viscosity. Further, the cap is detachable so that, even if the small aperture develops constriction or clogging due to mixing of a slime, suppuration, inflammation product, blood or the like into the mother's milk in a morbid case, the expression of the milk can still be continued by detaching the cap. The cap can also be washed with ease. The cap can of course be replaced by a cap with a small aperture having a greater diameter of from 5 mm to 6 mm. As the material of the cap, polypropylene resin or the like is effective.

Preferably, the teat cup liner is designed such that, when fitted in the teat cup, the teat cup liner is hermetically brought at a free end portion thereof and over an entire circumference thereof into close contact with an inner peripheral wall of the teat cup but a small space is formed at a portion of the teat cup liner other than the free end portion thereof between a back side of the teat cup liner and the inner peripheral wall of the teat cup. This design can make a stimulation, which is applied to the areola and nipple of the mother's breast upon production of a negative pressure, better simulate a suckling stimulation by an infant. Incidentally, negative pressures which occur at the free end of the teat cup liner at the time of expression of milk may preferably be between 0 mmHg and −200 mmHg.

The present invention will hereinafter be described based on the embodiment. FIG. 1 illustrates a breast pump 1 according to the present invention in its entirety in section, and FIG. 2 is a perspective view illustrating a teat cup liner 50. The breast pump 1 is composed of a collection container 2, a milk expressing member 10 attached to the collection container 2, and a negative pressure source 100 for producing a negative pressure and atmospheric pressure periodically at constant intervals.

The collection container 2 is a wide-mouthed container preferably made of polypropylene resin or an equivalent resin, and is provided with a cap 3 preferably of the screw-threaded type. The milk expressing member 10 according to the present invention is attached to the cap 3. Preferably, the milk expressing member 10 is also made of polypropylene resin or an equivalent resin in its entirety, and a main body section 11 which is in the form of a cylinder flares out at an end thereof in the form of a funnel to form a so-called teat cup 12 with an inner wall of which the breast is brought into contact. The main body section 11 is closed at an opposite end thereof by an end cover 13 which is preferably of the screw-threaded type. To the end cover 13, a connector plug 14 and a normally-closed relief valve 15 are attached although the latter is not essential. To the connector plug 14, a suitable tube which is connected with the negative pressure source 100 is attached so that by operation of the negative pressure source 100, a negative pressure and atmospheric pressure are periodically produced within the milk expressing member 10 and the collection container 2. The relief valve 15 is provided with a stem 17, which is equipped at a free end thereof with a sealing valve 16, and a spring 18 normally urging the stem 17 in such a direction that the sealing valve 16 is closed. In the event of an emergency or the like, the stem 17 is pressed to open the sealing valve 16 such that air is drawn through air inlets 16a formed on opposite sides to have the negative pressure returned to the atmospheric pressure inside the milk expressing member 16 and the collection container 2.

The main body section 11 of the milk expressing member 10 is provided at a substantially central part thereof with a cylindrical branch tube 20, and on the branch tube 20, a screw-threaded cap 3 for the collection container 2 is integrally attached by a suitable means. Therefore, threaded engagement of the cap 3 with a wide mouth portion of the collection container 2 integrates the collection container 2 and the milk expressing member 10 with each other, so that they are brought into a communicated state with the section of the branch tube 20 acting as a passageway. A partition plate 21 is arranged such that it extends through both of the branch tube 20 and the main body section 11. As illustrated in the drawing, the milk expressing member 10 is divided by the partition plate 21 into a space A communicated to the side of the teat cup 12 and a space B communicated to the connector plug 14.

A lower part of the branch tube 20 formed on the milk expressing member 10 extends through the cap 3 into the collection container 2. On the extension 22, a cap 30 made of a material such as polypropylene resin, for example, is detachably fitted. The cap 30 has an insert portion 30 into the branch tube 20, a shield plate 32 formed in a conical form integrally with a lower end portion of the insert portion 31, and a small aperture 33 formed through a central lower end portion of the shield plate 32. The small aperture 33 has a diameter of from about 1 mm to 3 mm or so and, in such an event that the breast pump 1 falls down, functions as a check valve to prevent the collected mother's milk from flowing backward. In some instances, a cap whose aperture has a greater diameter, for example, of from 5 mm to 6 mm or so may be used.

In the part of the teat cup 12 of the milk expressing member 10, a teat cup liner 50 is fitted in a replaceable state. The material of the teat cup liner 50 is preferably a silicone rubber, and as illustrated in the drawing, the teat cup liner 50 is formed of an insert portion 51 in a cylindrical form and a conical portion 52 flaring out in the form of a funnel from a free end of the insert portion 51. The insert portion 51 and the conical portion 52 are each in the form of a thin film, and the conical portion 52 is formed at a free end thereof into a thickened annular portion 53 which bulges out toward the back side. On the back sides of the insert portion 51 and conical portion 52, ridges 54 of substantially the same thickness as the thickened annular portion 53 are also formed integrally at predetermined intervals. The conical portion 52 is dimensioned large enough to substantially cover the area of the areola on the breast, and the inner diameter and length of the insert portion 51 in the cylindrical form are set such that the insert portion 51 can be brought into loose contact with the part of the nipple to envelope the same.

Ridge line portions of the ridges 54 formed on the back side of the insert portion 51 of the teat cup liner 50 are maintained in frictional engagement with the inner peripheral wall of the main body section 11 of the milk expressing member 10 so that in a state not separable freely, the teat cup liner 50 is fitted in the teat cup 12. The thickened annular portion 53 formed at the free end of the conical portion 52 and the ridges 54 formed on the back side of the conical portion 52 are also formed such that, when the teat cup liner 50 is fitted, they are both maintained at ridge line portions thereof in contact with the inner peripheral wall of the teat cup 12.

When the teat cup liner 50 is fitted in the teat cup 12, the teat cup liner 50 is brought into such a position that as illustrated in FIG. 1, only the ridge line portions of the thickened annular portion 53 and ridges 54 are maintained in contact with the inner peripheral walls of the teat cup 12 and main body section 11 and between the thin film making up the teat cup liner 50 and the inner peripheral walls of the teat cup 12 and main body section 11, air cells S are formed with their forward ends sealed by the thickened annular portion 53 and their rear ends kept open to the space A.

In the breast pump 1, the milk expressing member 10 with the teat cup liner 50 fitted in the teat cup 12 is assembled on the collection container 2 as shown in FIG. 1. When the teat cup 12 is gently pressed against the breast, the areola and nipple are brought into contact with the teat cup liner 50. As a consequence, the internal spaces of the collection container 1 and milk expressing member 10 are brought into a state isolated from the outside. When the negative pressure source 100 is connected to the connector plug 14 of the milk expressing member 10 and the negative pressure source 100 is actuated, a negative pressure is produced in the isolated spaces. Under the negative pressure, the teat cup liner 50 is deformed at its portions other than the thickened annular portion 53 and ridges 54, in other words, at its thin film portions toward the inner peripheral walls of the teat cup 12 and main body section 11.

When a negative pressure and atmospheric pressure are periodically applied from the negative pressure source 100 by a suitable control system, stimulations similar to suckling stimulations by an infant are applied to the areola and nipple of the mother's breast via the teat cup liner 50 so that smooth and universal expression of milk is feasible. The teat cup liner 50 is replaceable, so that provision of teat cup liners of different sizes in advance makes it possible to perform appropriate expression of milk from breasts of different sizes and shapes by simply replacing the teat cup liner.

FIG. 3 illustrates one example of the negative pressure source 100 which applies a negative pressure and atmospheric pressure periodically to the breast pump. This apparatus is equipped with a mechanical unit composed of a tube for connecting the mechanical unit to the connector plug arranged on the milk expressing member 10, solenoid valves, a vacuum pump and the like; a computer 150 for controlling the mechanical unit; and an operation and display unit 170 for the computer.

The mechanical unit is provided with a trap 102, a first two-way solenoid valve 103, and a negative pressure tank 104 capable of acting as a pressure-regulating tank or an accumulator, all of which are arranged in series between the tube 101, which is adapted to connect the mechanical unit to the connector plug 14, and the vacuum pump 110. Between the trap 102 and the first two-way solenoid valve 103, two branch tubes are arranged as first and second branch tubes 121,122. These branch tubers are provided with second and third two-way solenoid valves 123,124, respectively. Further, between the trap 102 and the first branch tube 121, third and fourth branch tubes 125,126 are arranged. These branch tubes 125,126 are provided at free ends thereof with first and second pressure sensors 127,128, respectively.

The computer 150 is connected with the second pressure sensor 128, the first and third solenoid valves 103,124 and the vacuum pump 110 to permit transmission of information, and controls inputs of pressure information from the pressure sensor 128, controlled outputs of on/off timings to the first and third solenoid valves 103,124, and outputs of actuation controls to the vacuum pump 110. The operation and display unit 170 is provided with an operation switch sub-unit 171 and a setting display sub-unit 172. The operation switch sub-unit 171 gives operation commands to the computer 150 as needed, and the state of operation or the like is displayed on the setting display sub-unit 172. An abnormal pressure detection circuit 180 is also arranged to detect signals from the first pressure sensor 127 arranged on the third branch tube 125 and, if any one of the signals is an abnormal value, an open signal is outputted to the second solenoid valve 123 arranged on the first branch tube 121.

A description will now be made of an illustrative operation of the negative pressure source 100. With the first, second and third solenoid valves 103,123,124 maintained in closed positions, the vacuum pump 110 is operated to produce a negative pressure within the negative pressure tank 104. After a predetermined pressure has been established, the first solenoid valve 103 is opened. As a result, the air inside the tube 101 and breast pump 1 is drawn into the negative pressure tank 104 so that the pressure inside the breast pump 1 is reduced from the atmospheric pressure to a predetermined negative pressure (preset pressure). At this time point, the first solenoid valve 103 is closed. As a consequence, the preset level of negative pressure is established and maintained within the breast pump 1, so that the teat cup liner 50 is deformed and suction, namely, expression of milk is performed.

After allowing the above state to continue for a predetermined time, the third solenoid valve 124 is opened. The interior of the breast pump 1 is hence brought into a state open to the atmosphere, so that its pressure returns to the atmospheric pressure. After allowing this state to continue for a predetermined time, the third solenoid valve 124 is closed and the first solenoid valve 103 is opened. This cycle is then repeated a preset number of times to proceed with expression of milk as desired. If any signal from the first pressure sensor 127 arranged on the third branch tube 125 indicates an abnormal value in the course of the suction, the abnormal pressure detection circuit 180 outputs an open signal to the second solenoid valve 123 arranged on the first branch tube 121 such that the pressure of the entire system is brought to the atmospheric pressure.

Figure 4:
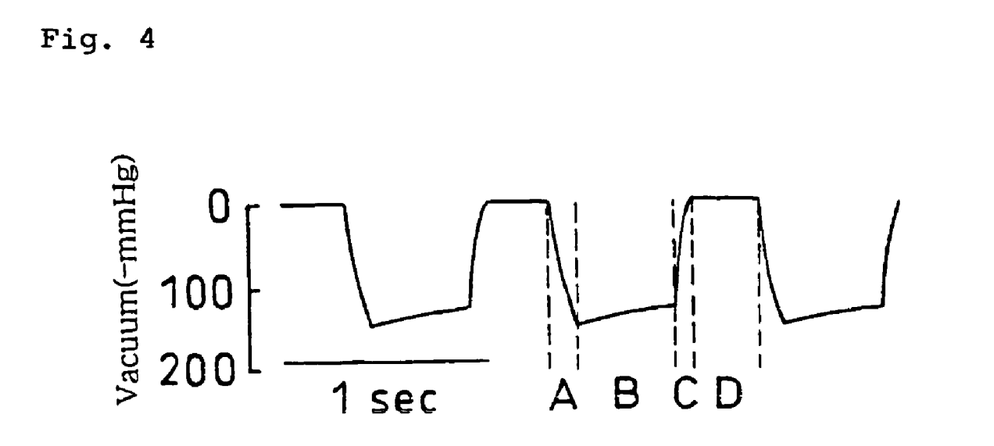
FIG. 4 is a diagram illustrating a pulsation characteristics curve (pulsogram) of the breast pump shown in FIG. 1.

A description will next be made of an example in which actual expression of milk was conducted by connecting the breast pump 1, which is depicted in FIG. 1, to the negative pressure source 100 shown in FIG. 3. FIG. 4 is a pulsation characteristics curve (pulsogram) obtained in the experiment, and Table 1 shows its analysis data. In FIG. 4 and Table 1, there are shown A: transition period (ultimate vacuum period), B: suction period, C: transition period (ultimate atmospheric pressure period), and D: atmospheric pressure period. A+B corresponds to a milk expressing period, and C+D corresponds to a pause period (massaging period).

TABLE 1

| Vacuum (−mmHg) | 140 |
| Pulsating rate (min)[a] | 60 |
| Percentage of pulsated periods (percentage of sucking periods)[b] | 60 |
| A (msec) | 120 |

TABLE 1-continued

| B (msec) | 480 |
| C (msec) | 80 |
| D (msec) | 320 |
| A + B (msec) | 600 |
| C + D (msec) | 400 |

[a] 60/A + B + C + D × 1000 (times/min)
[b] A + B/A + B + C + D × 100 (%)

INDUSTRIAL APPLICABILITY

As has been described above, the breast pump according to the present invention makes it possible to obtain universal data on an expressed sample of mother's milk without being affected by a personal difference. The breast pump is, therefore, a useful means especially in detecting any exogeneous toxic substance in the mother's milk. It has a simplified construction, so that the inside of its milk expressing member can be readily washed to avoid, with ease, inconveniences such as bacterial growth. Further, stimulations similar to suckling stimulations by an infant can be applied to the areola and nipple of the mother's breast, and therefore, smooth expression of milk is feasible.

The invention claimed is:

1. A breast pump including a collection container, a milk expressing member attachable to said collection container, and a negative pressure source configured to produce a negative pressure such that a pressure is periodically pulsated at constant intervals between said negative pressure and atmospheric pressure; said milk expressing member is provided at an end thereof with a teat cup, at an opposite end thereof with a connector plug to said negative pressure source, and between said teat cup and said connector plug with a passageway to said collection container; a partition plate is arranged in said passageway to divide said milk expressing member into a space communicated to said teat cup and a space communicated to said connector plug; and a teat cup liner is replaceably fitted in said teat cup, wherein said teat cup liner is dimensioned to be brought into contact with an areola and nipple of a breast and has such flexibility and resiliency that said teat cup liner undergoes a deformation toward said teat cup when exposed to said negative pressure but restores to an initial shape thereof when exposed to said atmospheric pressure.

2. A breast pump according to claim 1, wherein a cap, which is provided at a tip thereof with a small aperture capable of performing a function as a check valve, is detachably mounted on an outlet portion of said passageway to said collection container.

3. A breast pump according to claim 1 or 2, wherein a relief valve configured to promptly release said negative pressure from said breast pump is arranged on said milk expressing member on a side of said opposite end where said milk expressing member is provided with said connector plug to said negative pressure source.

4. A breast pump according to any one of claims 1–2, wherein a material of at least said teat cup is polypropylene resin or a material equivalent thereto, and a material of said teat cup liner is a silicone rubber.

5. A breast pump according to any one of claims 1–2, wherein said teat cup liner is designed such that, when fitted in said teat cup, said teat cup liner is hermetically brought at a free end portion thereof and over an entire circumference thereof into close contact with an inner peripheral wall of said teat cup but a small space is formed at a portion of said teat cup liner other than said free end portion thereof between a back side of said teat cup liner and said inner peripheral wall of said teat cup.

6. A breast pump according to any one of claims 1–2, wherein a negative pressure, which is produced at a free end of said teat cup liner upon expressing milk, is a negative pressure in a range of from 0 mmHg to 200 mmHg.

7. A breast pump according to any one of claims 1–2, wherein said negative pressure source is provided at least with a vacuum pump, a line for connecting said vacuum pump with said connector plug of said milk expressing member, a first two-way solenoid valve arranged on said line, a branch line arranged on said line on a side upstream of said first two-way solenoid valve, a second two-way solenoid valve arranged on said branch line, and a system controller for controlling on/off of at least said solenoid valves; and said branch line is open at a free end thereof to an atmosphere.

\* \* \* \* \*